US00PP16329P3

(12) United States Plant Patent
Coiner

(10) Patent No.: US PP16,329 P3
(45) Date of Patent: Mar. 14, 2006

(54) HYBRID TEA ROSE PLANT NAMED 'BRONZE SUNSET'

(50) Latin Name: *Rosa hybrida*
Varietal Denomination: Bronze Sunset

(75) Inventor: James W. Coiner, La Verne, CA (US)

(73) Assignee: Coiner Nursery, LaVerne, CA (US)

( * ) Notice: Subject to any disclaimer, the term of this patent is extended or adjusted under 35 U.S.C. 154(b) by 173 days.

(21) Appl. No.: 10/016,071

(22) Filed: Dec. 5, 2001

(65) Prior Publication Data

US 2003/0106115 P1 Jun. 5, 2003

(51) Int. Cl.
*A01H 5/00* (2006.01)

(52) U.S. Cl. ..... Plt./136

(58) Field of Classification Search ..... Plt./130, Plt./135, 136, 139
See application file for complete search history.

*Primary Examiner*—Howard J. Locker
(74) *Attorney, Agent, or Firm*—Christie, Parker & Hale, LLP

(57) ABSTRACT

A new and distinct Hybrid Tea Rose plant variety with orange flowers.

1 Drawing Sheet

Classification: The present invention relates to a new *Rosa hybrida* plant.

Variety denomination: The new plant has the varietal denomination 'Bronze Sunset'.

BACKGROUND OF THE INVENTION

The present invention relates to a new and distinct variety of rose plant of the hybrid tea rose of the genus *Rosaceae* which was created by crossing as seed and pollen parents two (2) unknown rose varieties. The varietal denomination of the new variety is 'Bronze Sunset'.

SUMMARY OF THE INVENTION

Among the novel characteristics possessed by this new variety which distinguishes it from other varieties of which I am aware, is its orange flowers.

Asexual reproduction by propagation by budding of the new variety onto 'Dr. Huey' rootstock as performed in Wasco, Calif. shows that the foregoing and other distinguishing characteristics come true to form and are established and transmitted through succeeding propagations.

BRIEF DESCRIPTION OF ILLUSTRATION

The accompanying illustration shows typical specimens of the flowers and foliage of the new variety depicted in color as nearly true as it is reasonably possible to make the same in a color illustration of this character.

DESCRIPTION OF THE NEW VARIETY

The following is a detailed description of 2-year budded plants of the new variety, with color terminology in accordance with The Royal Horticultural Society Colour Chart (R.H.S.C.C.). The terminology used in color description herein refers to plate numbers in the aforementioned color chart. Phenotypic expression may vary with light availability, environmental and cultural conditions.

The following observations are made of specimens grown outdoors in Wasco, Calif., during November budded on 'DR. HUEY' understock.

Plant:

*Form.*—Spreading.

*Growth.*—Vigorous; sprawling.

*Size.*—Height about 52 inches; width about 48 inches.

*Disease resistance.*—Cultivar exhibits average resistance/susceptibility to disease.

*Foliage.*—Size: Terminal leaflet length about 2½ inches; width about 1 9/16 inches. Quantity: Usually 5 compound leaflet leaves, occasionally compound 7 leaflet leaves. Color: New foliage: Upper side near 137B; under side near 148A. Mature foliage: Upper side near 139A; under side near 137B. Texture: Upper side: Smooth, semi-glossy. Under side: Matte. Edge: Serrated.

*Petioles.*—Top surface color near 138C; Under side near 138C.

*Stipules.*—Medium length.

*Auricle.*—Light red brown near 59C fading to green near 137B.

*Rachis.*—Few prickles.

Wood:

*New shoots.*—Bark: Smooth. Wood: Near 137C with anthocyanin blush near 59C.

*Old wood.*—Bark: Lots of prickles. Wood: Near 137D.

*Flowering stem.*—Length about 18 inches.

*Winter hardiness.*—Completely winter hardy.

*Preferred growing conditions.*—Likes full sun.

*Growth habit.*—Vigorous.

*Leaves per stem.*—About 5.

*Prickles/thorns.*—Mature wood bear large and small prickles, average quantity; about ⅛ inch×⅛ inch in size, with an occasional thorn as large as about ¼ inch×¼ inch, color near 149B slightly tipped with red at tip, base near 59A.

Flower/inflorescence:

*Blooming habit.*—Recurrent. Bud: About 1¼ inches long, 1½ inches wide. Form: Triangular. Color: Before sepals divide color near 169A; when sepals first divide color near 170B; when petals begin to unfurl color near 41A. Sepals: Size: About 1¼ inches in length, ¼ inch wide, small extensions, usually 5 sepals per bloom. Color: Topside near 164B; bottom near 137C. Peduncle: Length: About 2½ inches, typically with numerous small acicular appendages, slight anthocyanin in coloration, color near 57B. Strength: Strong. Color: Near 148C.

*Flower.*—Size: About 4¼ inches. Borne: Usually single with an occasional cluster. Form: Relative good form; high centered; unfurls to loose ruffled at maturity.

*Petalage.*—Petaloids in center: None. Persistence: Petals do not drop.

*Fragrance.*—Slight.

*Lasting quality.*—About 2 weeks on plant; about 6 days after cutting.

*Color.*—During first 2 days: Inner petals: (at flower center) topside and underside near 41A; base near 19A; Outer petals: Topside and underside near 43A, base near 16C.

*Base of petals* (*point of attachment*).—Near 17B.

*General tonality from a distance.*—Bronze.

*Color change.*—Darkens with age, color near 44C.

*Petals.*—Size: Length about 1¾ inches; width about 1½ inch. Texture: Thick, rigid. Shape: Wide at top, tapered to narrow bottom, petals reflexed to a point. Arrangement: Loose around pistils. Appearance: Satiny.

Reproductive organs:

*Arrangement of stamens, filaments and anthers.*—Near 163B; regularly arranged around styles, about 100 anthers and filaments.

*Color.*—Filaments near 162C; Anthers near 161C.

*Pollen.*—Near 168A.

*Styles.*—Bunched, uneven length.

*Stigmas.*—Color near 16C.

*Hips/seed vessels/ovaries.*—Shape: Oval. Size: About ½ inch. Color: Near 143B. Seeds: No seeds.

I claim:

1. A new and distinct Hybrid Tea Rose plant of the variety substantially as shown and described.

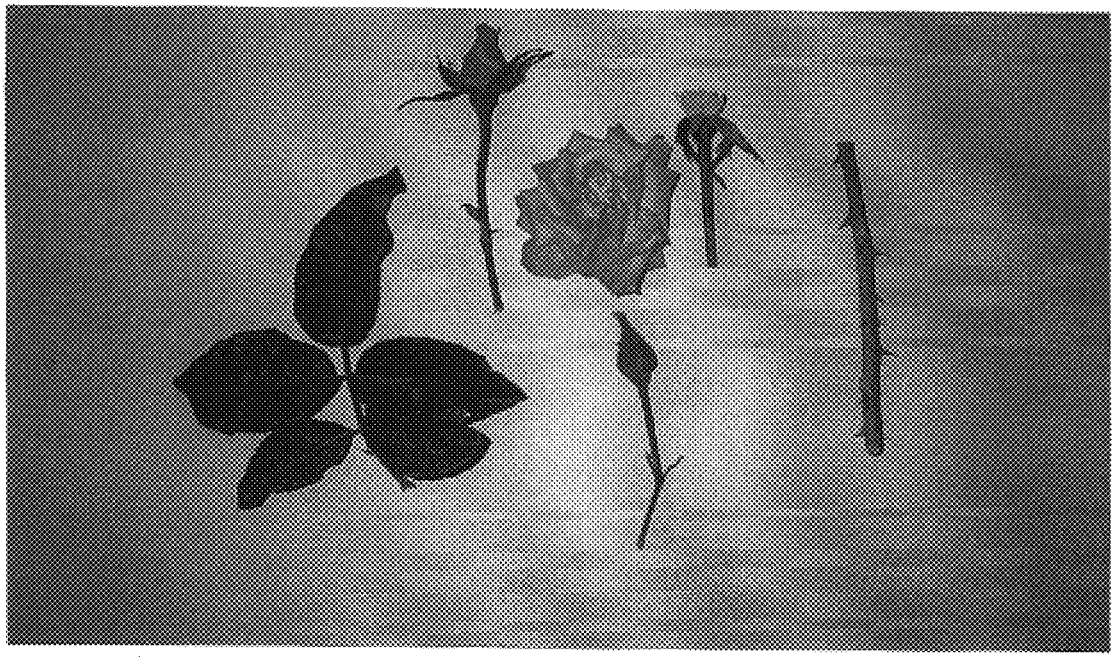

* * * * *